(12) United States Patent
Weckbecker

(10) Patent No.: US 6,362,164 B1
(45) Date of Patent: Mar. 26, 2002

(54) COMBINATION OF A SOMATOSTATIN ANALOGUE AND A RAPAMYCIN

(75) Inventor: Gisbert Weckbecker, Biel-Benken (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/194,957

(22) PCT Filed: Jun. 11, 1997

(86) PCT No.: PCT/EP97/03036

§ 371 Date: Dec. 7, 1998

§ 102(e) Date: Dec. 7, 1998

(87) PCT Pub. No.: WO97/47317

PCT Pub. Date: Dec. 18, 1997

(30) Foreign Application Priority Data

Jun. 11, 1996 (GB) ............................................. 9612171
Sep. 16, 1996 (GB) ............................................. 9619310

(51) Int. Cl.⁷ .................... A61K 38/31; A61K 38/08

(52) U.S. Cl. .............................. 514/16; 530/311; 514/2; 540/456

(58) Field of Search ............................................. 514/15

(56) References Cited

FOREIGN PATENT DOCUMENTS

| GB | 2 239 178 A | 6/1991 |
| WO | WO 93 11130 A | 6/1993 |

OTHER PUBLICATIONS

Shi E.A., Cancer Research, vol. 55, pp. 1982–19088 (1995). *

Grant et al., Circulation, vol. 89, No. 4, pp. 1511–1517 (1994).

Demoliou–Mason, Exp. Opin.Ther. Patents, vol. 4, No. 7, pp. 813–829 (1994).

*Primary Examiner*—Michael Borin
(74) *Attorney, Agent, or Firm*—Joseph J. Borovian

(57) ABSTRACT

A combination of a compound of the somatostatin class and a rapamycin macrolide is useful for the prevention or treatment of cell hyperproliferation.

13 Claims, No Drawings

COMBINATION OF A SOMATOSTATIN ANALOGUE AND A RAPAMYCIN

The present invention relates to a pharmaceutical combination and its use in the treatment of disorders associated with excess benign and malignant cell proliferation, e.g. tumors or intimal cell proliferation.

There is a continuing need for the development of drugs having increased effectiveness in inhibiting or slowing down undesired cell proliferation, particularly in the cancer field and in vasculopathies.

Accordingly, there is provided a pharmaceutical combination comprising a compound of the somatostatin class, and a rapamycin macrolide.

The somatostatin class is a known class of small peptides comprising the naturally occurring somatostatin-14 and analogues having somatostatin related activity, e.g. as disclosed by A. S. Dutta in Small Peptides, Vol. 19, Elsevier (1993). By "somatostatin analogue" as used herein is meant any straight-chain or cyclic polypeptide having a structure based on that of the naturally occurring somatostatin-14 wherein one or more amino acid units have been omitted and/or replaced by one or more other amino radical(s) and/or wherein one or more functional groups have been replaced by one or more other functional groups and/or one or more groups have been replaced by one or several other isosteric groups. In general, the term covers all modified derivatives of the native somatostatin-14 which exhibit a somatostatin related activity, e.g. they bind to at least one somatostatin receptor (hSST-1, hSST-2, hSST-3, hSST4 or hSST-5), preferably in the nMolar range, more preferably to at least the hSST-2 receptor in the nMolar range.

Cyclic, bridge cyclic and straight-chain somatostatin analogues or derivatives are known and have been described together with processes for their production e.g. in U.S. Pat. Nos. 4,310,518 and 4,235,886, in European Patent Specifications EP-A-1295; 23,192; 29,310; 29,579; 30,920; 31,303; 63,308; 70,021; 83,305; 215,171; 203,031; 214,872; 143,307; 298,732; 277,419; 389,180; 395,417; 450,480A2; in Belgian Patent Specification BE-A-900,089; and in WO 91/09056; WO 97/01579; WO 97/14715, the contents thereof, in particular with respect to the compounds, being incorporated herein by reference.

Preferred somatostatin analogues are e. g. compounds of formula I $$\begin{array}{c} \text{CH}_2\text{—S—Y}_1 \quad\quad \text{Y}_2\text{—S—CH}_2 \\ A' \\ \diagdown \\ N\text{—CH—CO—B—C—D—E—NH—CH—G} \\ \diagup \\ A \end{array} \quad (I)$$

wherein

A is $C_{1-12}$alkyl, $C_{7-10}$phenylalkyl or a group of formula RCO—, whereby
 i) R is hydrogen, $C_{1-11}$alkyl, phenyl or $C_{7-10}$phenylalkyl, or
 ii) RCO— is
 a) a D-phenylalanine residue optionally ring-substituted by halogen, $NO_2$, $NH_2$, OH, $C_{1-3}$alkyl and/or $C_{1-3}$alkoxy; or
 b) the residue of a natural or a synthetic α-amino-acid other than defined under a) above, or of a corresponding D-amino acid, or
 c) a dipeptide residue in which the individual amino acid residues are the same or different and are selected from those defined under a) and/or b) above, the α-amino group of amino acid residues a) and b) and the N-terminal amino group of dipeptide residues c) being optionally mono- or di-$C_{1-12}$alkylated or substituted by $C_{1-8}$alkanoyl;

A' is hydrogen or $C_{1-3}$alkyl, $Y_1$ and $Y_2$ represent together a direct bond or each of $Y_1$ and $Y_2$ is hydrogen B is -Phe- optionally ring-substituted by halogen, $NO_2$, $NH_2$, OH, $C_{1-3}$alkyl and /or $C_{1-3}$alkoxy (including pentafluoroalanine), naphthylalanine or pyridylalanine, C is (L)-Trp- or (D)-Trp- optionally α-N-methylated and optionally benzene-ring-substituted by halogen, $NO_2$, $NH_2$, OH, $C_{1-3}$alkyl and/or $C_{1-3}$alkoxy, D is Lys, 4-aminocyclohexylAla or 4-aminocyclohexylGly, E is Thr, Ser, Val, Tyr, Ile, Leu or an aminobutyric or aminoisobutyric acid residue, G is a group of formula $$-\text{COOR}_7, \quad -\text{CH}_2\text{OR}_{10}, \quad -\text{CON}\diagup^{R_{11}}_{\diagdown R_{12}} \quad \text{or}$$

$$-\text{CO}-\text{N}\underset{\phantom{X}}{\overset{R_{16}}{\diagup\diagdown}}\text{X}_1$$

wherein $R_7$ is hydrogen or $C_{1-3}$alkyl, $R_{10}$ is hydrogen or the residue of a physiologically acceptable, physiologically hydrolysable ester, e.g. formnyl, $C_{2-12}$alkylcarbonyl, benzoyl, $R_{11}$ is hydrogen, $C_{1-3}$alkyl, phenyl or $C_{7-10}$phenylalkyl $R_{12}$ is hydrogen, $C_{1-3}$alkyl or a group of formula —CH$(R_{13})$—$X_1$, $R_{13}$ is $CH_2OH$, —$(CH_2)_2$—OH, —$(CH_2)_3$—OH, —CH$(CH_3)$OH, isobutyl, butyl, benzyl, naphthyl-methyl or indol-3-yl-methyl, and $X_1$ is a group of formula $$-\text{COOR}_7, \quad -\text{CH}_2\text{OR}_{10} \quad \text{or} \quad -\text{CO}-\text{N}\diagup^{R_{14}}_{\diagdown R_{15}}$$

wherein $R_7$ and $R_{10}$ have the meanings given above, $R_{14}$ is hydrogen or $C_{1-3}$alkyl, $R_{15}$ is hydrogen, $C_{1-3}$alkyl, phenyl or $C_{7-10}$phenylalkyl, and $R_{16}$ is hydrogen or hydroxy, with the proviso that when $R_{12}$ is —CH$(R_{13})$—$X_1$, then $R_{11}$ is hydrogen or methyl, wherein the residues B, D and E have the L-configuration, and the residues in the 2- and 7-position each independently have the (L)- or (D)-configuration, in free form or in pharmaceutically acceptable salt or complex form.

Individual compounds of formula I suitable in accordance with the present invention are the following somatostatin analogues:

a. (D)Phe-Cys-Phe-(D)Trp-Lys-Thr-Cys-Thr-ol
also known as octreotide b. (D)Phe-Cys-Tyr-(D)Trp-Lys-Val-Cys-ThrNH₂ c. (D)Phe-Cys-Tyr-(D)Trp-Lys-Val-Cys-TrpNH₂
also known as vapreotide d. (D)Trp-Cys-Phe-(D)Trp-Lys-Thr-Cys-ThrNH₂ e. (D)Phe-Cys-Phe-(D)Trp-Lys-Thr-Cys-ThrNH₂ f. 3-(2-(Naphthyl)-(D)Ala-Cys-Tyr-(D)Trp-Lys-Val-Cys-ThrNH₂
also known as lanreotide g. (D)Phe-Cys-Tyr-(D)Trp-Lys-Val-Cys-β-Nal-NH₂ h. 3-(2-naphthyl)-Ala-Cys-Tyr-(D)Trp-Lys-Val-Cys-β-Nal-NH₂ i. (D)Phe-Cys-β-Nal-(D)Trp-Lys-Val-Cys-Thr-NH₂ j. (D)Phe-Cys-Tyr-(D)Trp-Lys-Leu-Cys-Thr-NH₂ k. (D)Phe-Cys-Tyr-(D)Trp-Lys-Cys-Thr-NH₂.

A preferred compound of formula I is octreotide.

Compounds of formula I may exist e.g. in free form, salt form or in the form of complexes thereof. Acid addition salts may be formed with e.g. organic acids, polymeric acids and inorganic acids. Such acid addition salt forms include e.g. the hydrochlorides and acetates. Complexes are e.g. formed from compounds of the invention on addition of inorganic substances, e.g. inorganic salts or hydroxides such as Ca- and Zn-salts, and/or on addition of polymeric organic substances.

Further somatostatin analogues suitable for use in accordance with the present invention are:

cyclo [-Asn-Phe-Phe-DTrp-Lys-Thr-Phe-Gaba-], cyclo (Asu-Lys-Asn-Phe-Phe-Trp-Lys-Thr-Tyr-Thr-Ser), and

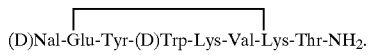
(D)Nal-Glu-Tyr-(D)Trp-Lys-Val-Lys-Thr-NH₂.

According to an alternatively preferred embodiment of the invention, the somatostatin component of the combination is a somatostatin analogue comprising the amino acid sequence of formula (II)

—(D/L)Trp-Lys-X₂—X₃—            (II)

wherein

X₂ is a radical of formula (a) or (b)

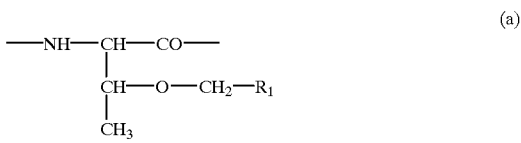

or

wherein

R₁ is optionally substituted phenyl,

R₂ is —Z₁—CH₂—R₁, —CH₂—CO—O—CH₂—R₁,

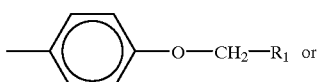

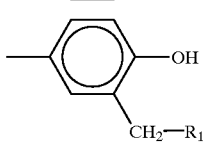

wherein

Z₁ is O or S, and

X₃ is an α-amino acid having an aromatic residue on the C$_\alpha$ side chain, or an amino acid unit selected from Dab, Dpr, Dpm, His,(Bzl)HyPro, thienyl-Ala, cyclohexyl-Ala and t.-butyl-Ala, the residue Lys of said sequence corresponding to the residue Lys[9] of the native somatostatin-14.

Such somatostatin analogues are e.g. disclosed in WO/97/01579, the contents thereof, in particular with respect to the specifically exemplified compounds, being incorporated herein by reference.

Preferably the sequence of formula II as defined above corresponds to the residues at positions 8 through 11 of the somatostatin-14. More preferably the somatostatin analogue as disclosed above comprises a hexapeptide unit, the residues at positions 3 through 6 of said hexapeptide unit comprising the sequence of formula II. More particularly the hexapeptide unit is cyclic, e.g. having a direct peptide linkage between the α-carbonyl group of the residue at position 6 and the α-amino group of the residue at position 1.

While Lys, X₂ and X₃ in the sequence of formula II have the L-configuration, Trp may have the D- or L-configuration, preferably the D-configuration.

X₂ is preferably a residue of formula (a) or (b), R₂ being preferably —Z₁—CH₂—R₁ or

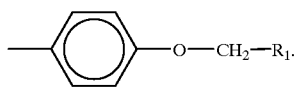

When $X_3$ comprises an aromatic residue on the $C_\alpha$ side chain, it may suitably be a natural or unnatural α-amino acid, e.g. Phe, Tyr, Trp, Nal, Pal, benzothienyl-Ala, Tic and thyronin, preferably Phe or Nal, more preferably Phe. $X_3$ is preferably an α-amino acid bearing an aromatic residue on the $C_\alpha$ side chain.

When $R_1$ is substituted phenyl, it may suitably be substituted by halogen, methyl, ethyl, methoxy or ethoxy e.g. in ortho and/or position. More preferably $R_1$ is unsubstituted phenyl. $Z_1$ is preferably O.

Representative somatostatin analogues comprising a residue of formula II are e.g compounds of formula (III)

(II)

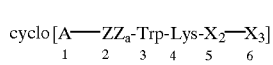

wherein $X_2$ and $X_3$ are as defined above, $A_1$ is a divalent residue selected from Pro,

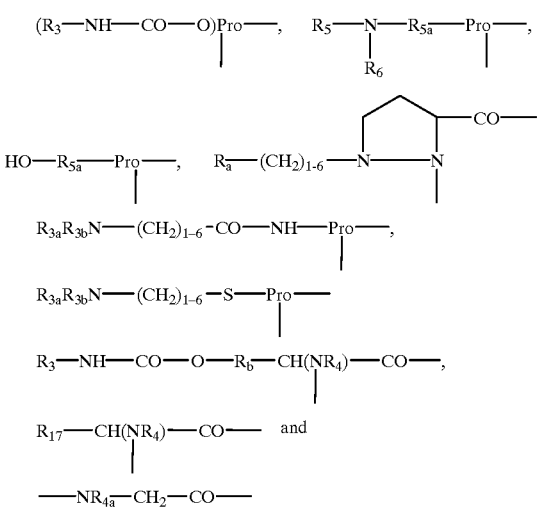

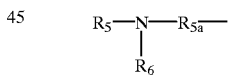

wherein $R_3$ is $NR_8R_9$—$C_{2-6}$alkylene, guanidino-$C_{2-6}$alkylene or $C_{2-6}$alkylene-COOH, $R_{3a}$ is H, $C_{1-4}$alkyl or has independently one of the significances given for $R_3$ $R_{3b}$ is H or $C_{1-4}$alkyl, $R_a$ is OH or $NR_5R_6$, $R_b$ is —$(CH_2)_{1-3}$— or —$CH(CH_3)$—, $R_4$ is H or $CH_3$, $R_{4a}$ is optionally ring-substituted benzyl, each of $R_5$ and $R_6$ independently is H, $C_{1-4}$alkyl, ω-amino-$C_{1-4}$alkylene, ω-hydroxy-$C_{1-4}$alkylene or acyl, $R_{5a}$ is a direct bond or $C_{1-6}$alkylene, each of $R_8$ and $R_9$ independently is H, $C_{1-4}$alkyl, ω-hydroxy-$C_{2-4}$alkylene, acyl or $CH_2OH$—$(CHOH)_c$—$CH_2$— wherein c is 0, 1, 2, 3 or 4, or $R_8$ and $R_9$ form together with the nitrogen atom to which they are attached a heterocyclic group which may comprise a further heteroatom, and $R_{17}$ is optionally ring-substituted benzyl, —$(CH_2)_{1-3}$—OH, $CH_3$—CH(OH)— or —$(CH_2)_{1-5}$—$NR_5R_6$, and $ZZ_a$ is a natural or unnatural α-amino acid unit.

$ZZ_a$ may have the D- or L-configuration. When $ZZ_a$ is a natural or unnatural α-amino acid unit, it may suitably be e.g. Thr, Ser, Ala, Val, Ile, Leu, Nle, His, Arg, Lys, Nal, Pal, Tyr, Trp, optionally ring-substituted Phe or $N^\alpha$-benzyl-Gly. When $ZZ_a$ is Phe, the benzene ring thereof may be substituted by e.g. $NH_2$, $NO_2$, $CH_3$, $OCH_3$ or halogen, preferably in para position. When $ZZ_a$ is Phe, the benzene ring thereof is preferably unsubstituted.

When $A_1$ comprises a Pro amino acid residue, any substituent present on the proline ring, e.g. $R_3$—NH—CO—O— etc., is preferably in position 4. Such substituted proline residue may exist in the cis form, e.g.

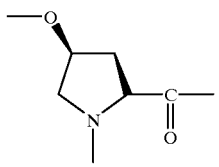

as well as in the trans form. The present invention covers each geometric isomer individually as well as mixtures thereof.

When $A_1$ is ($NR_8R_9$—$C_{6-2}$alkylene-NH—CO—)Pro-where $NR_8R_9$ forms a heterocyclic group, such group may be aromatic or saturated and may comprise one nitrogen or one nitrogen and a second heteroatom selected from nitrogen and oxygen. Preferably the heterocyclic group is e.g. pyridyl or morpholino. $C_{2-6}$Alkylene in this residue is preferably —$CH_2$—$CH_2$—.

Any acyl as $R_5$, $R_6$, $R_8$ and $R_9$ in $A_1$ may be e.g. $R_{18}CO$— wherein $R_{18}$ is H, $C_{1-4}$alkyl, $C_{2-4}$alkenyl, $C_{3-6}$cycloalkyl or benzyl, preferably methyl or ethyl. When $R_{4a}$, or $R_{17}$ in $A_1$ is ring-substituted benzyl, the benzene ring may be substituted as indicated above for $ZZ_a$.

A preferred group of compounds of formula III are such wherein $A_1$ is free of a lateral —NH—CO—O— moiety. A further group of preferred compounds of formula III are such wherein $A_1$ comprises a basic lateral radical, e.g. a $R_3$—NH—CO—O— or moiety.

A still further group of preferred compounds of formula III are such wherein the N-terminal amino acid comprises a substituted Pro, particularly 4-substituted Pro, e.g. compounds of formula III wherein $A_1$ is 4-substituted Pro.

Preferably $A_1$ is 4-($R_3$—NH—CO—O)Pro.

Examples of somatostatin analogues comprising a residue of formula II include e.g. cyclo [4—($NH_2$—$C_2H_4$—NH—CO—O—)Pro-Phe-DTrp-Lys-Ser(Benzyl)-Phe].

The term "macrolide" as used herein, refers to a macrocyclic lactone, for example a compound having a 12-membered or larger lactone ring. Of particular interest are the "lactam macrolides", i.e. macrocyclic compounds having a lactam (amide) bond in the macrocycle in addition to a lactone (ester) bond, for example rapamycin and its numerous derivatives and analogues. Rapamycin is an immunosuppressive lactam macrolide that is produced by

*Streptomyces hygroscopicus,* and having the structure depicted in Formula (A)

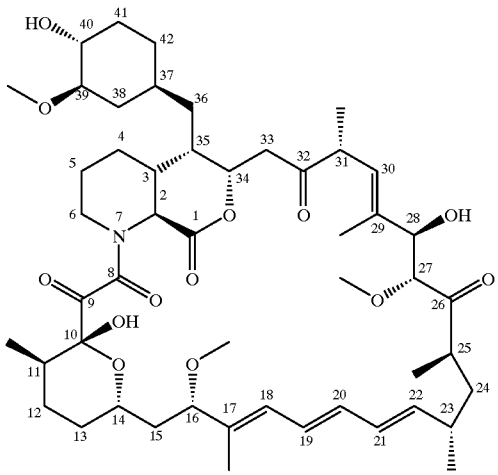

See, e.g., McAlpine, J. B., et al., J. Antibiotics (1991) 44: 688; Schreiber, S. L., et al., J. Am. Chem. Soc. (1991) 113: 7433; U.S. Pat. No. 3 929 992. One group of rapamycin derivatives are 40-0-substituted derivatives of rapamycin having the structure of Formula IV:

IV

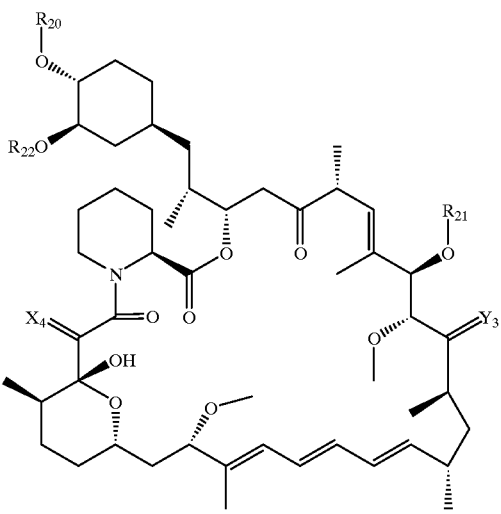

wherein
$X_4$ is (H,H) or O;
$Y_3$ is (H,OH) or O;
$R_{20}$ and $R_{21}$ are independently selected from H, alkyl, arylalkyl, hydroxyalkyl, dihydroxyalkyl, hydroxyalkoxycarbonylalkyl, hydroxyalkylarylalkyl, dihydroxyalkylarylalkyl, acyloxyalkyl, aminoalkyl, alkylaminoalkyl, alkoxycarbonylaminoalkyl, acylaminoalkyl, arylsulfonamidoalkyl, allyl, dihydroxyalkylallyl, dioxolanylallyl, dialkyl-dioxolanylalkyl, di(alkoxycarbonyl)-triazolyl-alkyl and hydroxyalkoxy-alkyl; wherein "alk-" or "alkyl" refers to $C_{1-6}$alkyl, branched or linear, preferably $C_{1-3}$alkyl,; "aryl" is phenyl or tolyl; and acyl is a radical derived from a carboxylic acid; and $R_{22}$ is methyl or $R_{22}$ and $R_{20}$ together form $C_{2-6}$alkyl; provided that $R_{20}$ and $R_{21}$ are not both H; and hydroxyalkoxyalkyl is other than hydroxyalkoxymethyl.

Such compounds are disclosed in WO 94/09010 the contents of which, in particular with respect to the specifically exemplified compounds, are incorporated herein by reference.

A preferred compound is e.g. 40-O-(2-hydroxy)ethyl-rapamycin (referred thereafter as Compound B).

Further preferred rapamycin derivatives are e.g. those disclosed in WO 96/41807, the contents thereof, in particular with respect to the specifically exemplified compounds of formula I disclosed therein, being incorporated herein by reference. Particularly preferred are 32-deoxo-rapamycin, 16-O-pent-2-ynyl-32-deoxo-rapamycin, 16-O-pent-2-ynyl-32-deoxo-40-O-(2-hydroxyethyl)-rapamycin, 16-O-pent-2-ynyl-32-(S)-dihydro-rapamycin and 1 6-O-pent-2-ynyl-32-(S)-dihydro-40-O-(2-hydroxyethyl)-rapamycin.

Further rapamycin derivatives are known, e.g. carboxylic acid esters such as disclosed in WO 92/05179, amide esters such as disclosed in U.S. Pat. No. 5,118,677, carbamates such as described in U.S. Pat. No. 5,118,678, fluorinated esters such as disclosed in U.S. Pat. No. 5,100,883, acetals, e.g. in U.S. Pat. No. 5,151,413, silyl ethers, e.g. in U.S. Pat. No. 5,120,842, arylsulfonates and sulfamates, e.g. in U.S. Pat. No. 5 177 203, derivatives wherein the methoxy group at the position 16 is replaced with alkynyloxy, e.g. in WO 95/16691 and further derivatives such as disclosed in WO 93/11130, WO 94/02136, WO 94/02385 and WO 95/14023, all incorporated herein by reference.

Rapamycin and above mentioned derivatives have been shown to have potent immunosuppressant properties. Rapamycin has also been shown to inhibit smooth muscle cell proliferation and to inhibit cancer growth.

Somatostatin analogues, e.g. octreotide, vapreotide and lanreotide, have been disclosed i.a. to inhibit growth hormone secretion and to have an inhibiting effect on malignant tumor growth, e.g. in breast cancer. Octreotide and lanreotide have also been disclosed to inhibit smooth muscle cell proliferation.

In accordance with the invention, it has now surprisingly been found that a combination of 2 active ingredients believed to act on basically different mechanisms such as a somatostatin analogue and rapamycin or a derivative thereof, can be combined and synergistically inhibit cell hyperproliferation.

In accordance with the particular findings of the present invention, there is provided in a first aspect:

1. Use of a compound of the somatostatin class, in free form or in pharmaceutically acceptable salt form, for manufacturing a pharmaceutical composition for use in synergistically effective amounts in the prevention or treatment of cell hyperproliferation in combination with a rapamycin macrolide, e.g. for the manufacture of a kit as disclosed hereinafter.

2. Use of a compound of the somatostatin class, in free form or in pharmaceutically acceptable salt form, in combination in synergistically effective amounts with a rapamycin macrolide for the prevention or treatment of cell hyperproliferation.

3. A method for preventing or treating cell hyperproliferation in a subject in need of such treatment which comprises administering to such subject a synergistically effective amount of a compound of the somatostatin class in free form or in pharmaceutically acceptable salt form, and a rapamycin macrolide.

4. A kit or package for the treatment or prevention of cell hyperproliferation, said kit or package including a pharmaceutical composition comprising a compound of the somatostatin class in free form or in pharmaceutically acceptable salt form, and a pharmaceutical composition comprising a rapamycin macrolide. The kit or package may also contain instructions to use the pharmaceutical compositions in accordance with the present invention.

According to the invention, the combination of a compound of the somatostatin class and a rapamycin macrolide is indicated for the prevention or treatment of malignant tumor growth, e.g. breast, lung, GEP tumors, pituitary adenomas, lymphomas, etc., for the prevention or treatment of proliferative vascular diseases, e.g. biologically or mechanically induced vascular injury causing intimal thickening, e.g. restenosis, atherosclerosis, vascular occlusion, injury following percutaneous transluminal coronary angioplasty, vascular surgery or transplantation surgery, transplant vasculopathies, for example chronic rejection of various tissues and organs such as heart, kidney, pancreas, lung, liver, bowel, trachea and combined heart-lung.

The combination is particularly indicated for preventing intimal smooth muscle cell hyperplasia, restenosis and vascular occlusion in a mammal.

Utility of the combination in the treatment of disorders and diseases as hereinbefore specified, may be demonstrated for example in accordance with the method hereinafter described.

A. In vitro Assay

AR42J cell cultures are propagated in DMEM supplemented with 10% fetal calf serum (FCS) at 5% $CO_2$. Cells are grown in the absence of antibiotics or antifungal agents. Subconfluent AR42J cells growing in DMEM and supplemented with 10% FCS are trypsinized, diluted in DMEM+ 2.5% FCS and seeded in uncoated 96-well plates (5,000 to 10,000 cells per well in 180 $\mu$l). After a 48-hr incubation period (Day O), the number of cells in a separate control plate is determined both by counting cells in a Coulter counter and by the sulforhodamine B (SRB) staining assay. The cells are then exposed either to the somatostatin analogue alone, e.g. octreotide, or to rapamycin or a derivative thereof alone or to a combination of the somatostatin analogue and rapamycin or its derivative up to 5 days at various concentrations. Total drug exposure lasts for up to 5 days following the first addition and SRB analysis as described above is performed e.g. on day 2 and day 5. Growth is determined as difference in absorbance (OD) between day 0 and day x values (=delta OD). Calculations are made based on the fractional product method of Webb (Valeriote and Lin, 1975; Cory and Carter, 1986; Berenbaum, J. Theor. Biol. 114: 413–431, 1985) and the method by Chou and Talalay (Adv. Enz. Regul. 22: 27–55, 1984). If the measured cell growth (% of control) is <compared to the calculated cell growth, this shows evidence for a synergistic effect. Under these conditions a combination of a somatostatin analogue at a concentration of from $10^{-10}$ to $10^{-6}$ M with a rapamycin macrolide thereof at a concentration of from 1 to 1000 nM significantly inhibits the growth of the tumor cells.

In this assay, the following results are obtained with octreotide alone, Compound B alone and a combination of octreotide and Compound B. The synergy according to the Webb Method is confirmed by using the Chou-Talalay Method.

| | | Cell Growth (% of CONTROL) | | |
|---|---|---|---|---|
| | Concentration (nM) | Cell Growth ($\Delta$OD) (%) | Observed (%) | Calculated (Webb Method) (%) |
| Control | | 664 ± 9 | 100 | |
| Octreotide | 1.2 | 397 ± 16 | 59.8 | |
| Compound B | 12.0 | 420 ± 12 | 63.3 | |
| Octreotide + Compound B | 1.2 + 12.0 | 103 ± 5 | 15.6 | 37.9 |

B. In Vivo Assay

The AR42J (AR4-2J) rat pancreatic tumor cell line is derived from an azaserine-induced exocrine pancreatic tumor (Jessop and Hay, 1980). It was obtained from ATCC. Cultures are propagated in DMEM supplemented with 10% fetal calf serum (FCS) at 5% $CO_2$. Cells are grown in the absence of antibiotics or antifungal agents. Female nude mice (nu/nu Balbc-A from Iffa Credo, Lyon, France) weighing 19–22 g, are kept in groups of 5 animals in macrolon cages (type III, 16×22×11 cm). The cages are placed in ventilated cabinets (Iffa Credo) that are maintained at 24±1° C. The animals have free access to drinking water and a pathogen-free rodent diet (Diet A, Kliba, Basel, Switzerland). To initiate tumors from cultured cells, AR42J cells are trypsinized and 10×10$^6$ tumor cells (in 0.2 ml) are injected subcutaneously (s.c.) into both flanks of nude mice. When tumors have reached a volume of 0.03 cm$^3$, animals are randomized into control and treatment groups. Control animals receive placebo. Animals are treated as indicated below for 3 weeks with single agents or the drug combination. The somatostatin analogue is given as a single injection of a slow release form at 30 mg/kg s.c. The size of the tumors is determined with a caliper. To calculate the tumor volume in ml, the equation "volume (ellipsoid)=length× depth×height×0.52" was used.

Results

After 4 weeks, the following tumor sizes were determined.

(Please note that values in the control group correspond to 3 week values, since animals were killed afterwards for tumors that became excessively large.)

| Treatment | Volume mm$^3$ | SE |
|---|---|---|
| Control | 4020 | 579 |
| A) Compound B, 5 mg/kg p.o. | 3685 | 263 |
| B) Rapamycin, 5 mg/kg p.o. | 2748 | 325 |
| C) Octreotide pamoate (biodegradable, sustained release formulation), 30 mg/kg, single inj. | 2205 | 339 |
| Compound B + octreotide (C) | 130 | 75 |
| Rapamycin + octreotide (C) | 106 | 44 |

C. Clinical trial

Patients are included who have breast cancer as evidenced by histological biopsy (glandular analysis—EOA). They present a metastatic illness and/or loco-regional localization which is measurable and evaluable. If desired, patients may be included who are resistant to other treatment to conventional therapy such as surgery, radiotherapy, other chemotherapy and/or hormone therapy.

The patients present at least one target, on X-ray analysis, which is measurable or evaluable such as a primitive metastatic tumor which is cutaneous or sub-cutaneous. It may be gangliar or visceral. Preferably, the patients have lesions which have progressed within the month preceding the trial and have an estimated survival time of at least 3 months.

The rapamycin macrolide, e.g rapamycin or compound B is administered orally. The treatment is for at least 3 months or until complete remission. The response may be followed by conventional methodology, e.g. according to IUCC response criteria, e.g. progression, stabilization, partial or complete remission.

The somatostatin analogue, e.g. octreotide, is administered parenterally, e.g. subcutaneous, particularly in a continuous subcutaneous way by means of a portable syringe pump (infusion pump).

According to the invention, the somatostatin analogue and the rapamycin macrolide are preferably administered in the form of a pharmaceutical composition. Rapamycin and its derivatives, e.g. Compound B, may be administered by any conventional route, in particular enterally, e.g. orally, e.g. in the form of tablets, capsules, drink solutions, emulsions or microemulsion preconcentrates, nasally, pulmonary (by inhalation), parenterally, e.g. in the form of injectable solutions or suspensions, or topically. Rapamycin and its derivatives are preferably administered per os and the somatostatin analogue is preferably administered parenterally, e.g by infusion. The somatostatin analogue may also be administered in a slow release form, e.g. as disclosed in UK Patent Specification 2,265,311B. The administration of each component of the combination may take place either separately, simultaneously or sequentially, e.g. rapamycin or Compound B may be administered at first followed later, e.g. 8 to 24 hours later, by the somatostatin analogue.

The amount of each component administered is determined taking into account various factors such as the etiology and severity of the disease, and the patient's condition. Rapamycin or its derivatives may conveniently be administered at doses which are in the range used in immunosuppressive applications such as prevention and treatment of graft vs. host disease, transplant rejection or autoimmune diseases e.g. at a daily dosage from about 0.5 to 500 mg as a single dose or in divided doses. Such doses may also be given intermittently, for example, every other day or every third day. The somatostatin analogue may be administered, e.g. subcutaneously, in a dosage range of about 100 μg to 10 mg per day as a single dose or in divided doses. Thus octreotide may be administered at a dose of from 0.2 mg to 10 mg twice or three times daily. When administered as a slow release form, such formulation may comprise the somatostatin peptide in a concentration from 2.0 to 10% by weight. The release period of such a formulation may be from 1 week to about 2 months. The combination of the somatostatin analogue with rapamycin or its derivative allows to maximize the antiproliferative effect.

The invention contemplates that the active ingredients discussed herein may be utilized in combination with pharmaceutically acceptable diluents and carriers.

FORMULATION EXAMPLES

A. Somatostatin Formulations

1. Ampoules

| Octreotide | 0.5 mg |
| Mannitol | 45.0 mg |
| Lactic acid (88%) | 3.4 mg |
| Sodium hydrogenocarbonate | to pH 4.2 |
| Water (inject. grade) | to 1 ml |
| Carbon dioxide | q.s. |

2. Biodegradable Sustained Release Formulation

| Octreotide Acetate | 4.65% (by weight) |
| Poly(DL-lactide-co-glycolide) | 78.35% |
| Sterile Mannitol | 17% |
| Vehicle | |
| Carboxymethylcellulose | 0.5% (by weight) |
| Mannitol | 0.6% |
| Water for injection | 98.9% |

B. Rapamycin (or Derivative thereof) Formulation: e.g. Capsules

| Ethanol | 20.0 mg |
| 1,2-propylene glycol | 81.0 mg |
| Refined oil | 121.5 mg |
| Cremophor RH40 | 202.5 mg |
| Rapamycin or Compound B | 20.0 mg |
| Total | 500 mg |

What is claimed is:

1. A kit or package for the inhibition of cell hyperproliferation, said kit or package including a pharmaceutical composition comprising an analogue of somatostatin-14 binding to at least the hSST-2 receptor in the nMolar range selected from a) (D)Phe-Cys-Phe-(D)Trp-Lys-Thr-Cys-Thr-ol b) (D)Phe-Cys-Tyr-(D)Trp-Lys-Val-Cys-ThrNH$_2$ c) (D)Phe-Cys-Tyr-(D)Trp-Lys-Val-Cys-TrpNH$_2$ d) (D)Trp-Cys-Phe-(D)Trp-Lys-Thr-Cys-ThrNH$_2$ e) (D)Phe-Cys-Phe-(D)Trp-Lys-Thr-Cys-ThrNH$_2$ f) 3-(2-(Naphthyl)-(D)Ala-Cys-Try-(D)Trp-Lys-Val-Cys-ThrNH$_2$ g) (D)Phe-Cys-Tyr-(D)Trp-Lys-Val-Cys-β-Nal-NH$_2$ h) 3-(2-(naphthyl)-Ala-Cys-Tyr-(D)Trp-Lys-Val-Cys-β-Nal-NH₂
   |_____| i) (D)Phe-Cys-β-Nal-(D)Trp-Lys-Val-Cys-Thr-NH₂
   |_____| j) (D)Phe-Cys-Tyr-(D)Trp-Lys-Leu-Cys-Thr-NH₂ and
   |_____| k) (D)Phe-Cys-Tyr-(D)Trp-Lys-Cys-Thr-NH₂,
   |_____| in free form or in pharmaceutically acceptable salt form, and a pharmaceutical composition comprising a rapamycin macrolide selected from rapamycin and 40-O-(2-hydroxyethyl)-rapamycin, said compositions being present in synergistic effective amounts, together with instructions for use.

2. A kit or package according to claim 1 wherein the analogue of somatostatin-14 is selected from a) (D)Phe-Cys-Phe-(D)Trp-Lys-Thr-Cys-Thr-ol
   |_____| c) (D)Phe-Cys-Tyr-(D)Trp-Lys-Val-Cys-ThrNH₂, and
   |_____| f) 3-(2-(Naphthyl)-(D)Ala-Cys-Tyr-(D)Trp-Lys-Val-Cys-ThrNH₂,
   |_____| in free form or pharmaceutically acceptable salt form.

3. A kit or package according to claim 2 wherein the analogue of somatostatin-14 is (D)Phe-Cys-Phe-(D)Trp-Lys-Thr-Cys-Thr-ol
|_____| in free form or in pamoate salt form.

4. A kit or package according to claim 3 wherein the somatastatin-14 analogue is in sustained release form and the rapamycin macrolide is 40-O-(2-hydroxyethyl)-rapamycin.

5. A kit or package according to claim 1 for simultaneous or sequential use in synergistically effective amounts.

6. A pharmaceutical composition comprising a pharmaceutically acceptable carrier and a therapeutically effective amount of: 1) an analogue of somatostatin-14 binding to at least the hSST-2 receptor in the nMolar range selected from a) (D)Phe-Cys-Phe-(D)Trp-Lys-Thr-Cys-Thr-ol
   |_____| b) (D)Phe-Cys-Tyr-(D)Trp-Lys-Val-Cys-ThrNH₂
   |_____| c) (D)Phe-Cys-Tyr-(D)Trp-Lys-Val-Cys-TrpNH₂
   |_____| d) (D)Trp-Cys-Phe-(D)Trp-Lys-Thr-Cys-ThrNH₂
   |_____| e) (D)Phe-Cys-Phe-(D)Trp-Lys-Thr-Cys-ThrNH₂
   |_____| f) 3-(2-(Naphthyl)-(D)Ala-Cys-Try-(D)Trp-Lys-Val-Cys-ThrNH₂
   |_____| g) (D)Phe-Cys-Tyr-(D)Trp-Lys-Val-Cys-β-Nal-NH₂
   |_____| h) 3-(2-(naphthyl)-Ala-Cys-Tyr-(D)Trp-Lys-Val-Cys-β-Nal-NH₂
   |_____| i) (D)Phe-Cys-β-Nal-(D)Trp-Lys-Val-Cys-Thr-NH₂
   |_____| j) (D)Phe-Cys-Tyr-(D)Trp-Lys-Leu-Cys-Thr-NH₂ and
   |_____| k) (D)Phe-Cys-Tyr-(D)Trp-Lys-Cys-Thr-NH₂,
   |_____| in free form or pharmaceutically acceptable salt form; and 2) a rapamycin macrolide selected from rapamycin and 40-O-(2-hydroxyethyl)-rapamycin, said somatastatin-14 analogue and macrolide being present in synergistic effective amounts.

7. A composition according to claim 6 wherein the analogue of somatostatin-14 is selected from a) (D)Phe-Cys-Phe-(D)Trp-Lys-Thr-Cys-Thr-ol
   |_____| c) (D)Phe-Cys-Tyr-(D)Trp-Lys-Val-Cys-ThrNH₂, and
   |_____| f) 3-(2-(Naphthyl)-(D)Ala-Cys-Tyr-(D)Trp-Lys-Val-Cys-ThrNH₂,
   |_____| in free form or pharmaceutically acceptable salt form.

8. A composition according to claim 7 wherein the analogue of somatastatin-14 is (D)Phe-Cys-Phe-(D)Trp-Lys-Thr-Cys-Thr-ol
|_____| in free form or in pamoate salt form.

9. A composition according to claim 8 wherein the somatostatin-14 analogue is in sustained release form and the rapamycin macrolide is 40-O-(2-hydroxyethyl)-rapamycin.

10. A method of inhibiting cell hyperproliferation comprising administering to a subject in need of such treatment a therapeutically effective amount of: 1) an analogue of somatostatin-14 binding to at least the hSST-2 receptor in the nMolar range selected from a) (D)Phe-Cys-Phe-(D)Trp-Lys-Thr-Cys-Thr-ol
   |_____| b) (D)Phe-Cys-Tyr-(D)Trp-Lys-Val-Cys-ThrNH$_2$ c) (D)Phe-Cys-Tyr-(D)Trp-Lys-Val-Cys-TrpNH$_2$ d) (D)Trp-Cys-Phe-(D)Trp-Lys-Thr-Cys-ThrNH$_2$ e) (D)Phe-Cys-Phe-(D)Trp-Lys-Thr-Cys-ThrNH$_2$ f) 3-(2-(Naphthyl)-(D)Ala-Cys-Try-(D)Trp-Lys-Val-Cys-ThrNH$_2$ g) (D)Phe-Cys-Tyr-(D)Trp-Lys-Val-Cys-β-Nal-NH$_2$ h) 3-(2-(naphthyl)-Ala-Cys-Tyr-(D)Trp-Lys-Val-Cys-β-Nal-NH$_2$ i) (D)Phe-Cys-β-Nal-(D)Trp-Lys-Val-Cys-Thr-NH$_2$ j) (D)Phe-Cys-Tyr-(D)Trp-Lys-Leu-Cys-Thr-NH$_2$ and k) (D)Phe-Cys-Tyr-(D)Trp-Lys-Cys-Thr-NH$_2$, in free form or pharmaceutically acceptable salt form; and 2) a rapamycin macrolide selected from rapamycin and 40-O-(2-hydroxyethyl)-rapamycin, said somatostatin-14 analogue and macrolide being present in synergistic effective amounts.

11. A method according to claim 10 herein the analogue of somatostatin-14 is selected from a) (D)Phe-Cys-Phe-(D)Trp-Lys-Thr-Cys-Thr-ol c) (D)Phe-Cys-Tyr-(D)Trp-Lys-Val-Cys-ThrNH$_2$, and f) 3-(2-(Naphthyl)-(D)Ala-Cys-Tyr-(D)Trp-Lys-Val-Cys-ThrNH$_2$, in free form or pharmaceutically acceptable salt form.

12. A method according to claim 11 wherein the analogue of somatastatin-14 is (D)Phe-Cys-Phe-(D)Trp-Lys-Thr-Cys-Thr-ol in free form or in pamoate salt form.

13. A method according to claim 12 wherein the somatostatin-14 analogue is in sustained release form and the rapamycin macrolide is 40-O-(2-hydroxyethyl)-rapamycin.

* * * * *

UNITED STATES PATENT AND TRADEMARK OFFICE
CERTIFICATE OF CORRECTION

PATENT NO. : 6,362,164 B1
DATED : March 26, 2002
INVENTOR(S) : Gisbert Weckbecker It is certified that error appears in the above-identified patent and that said Letters Patent is hereby corrected as shown below:

Column 13,
Item c) should read:
-- c) (D)Phe-Cys-Tyr-(D)Trp-Lys-Val-Cys-TrpNH$_2$, and --

Signed and Sealed this

Twenty-sixth Day of November, 2002

Attest:

JAMES E. ROGAN
Attesting Officer   Director of the United States Patent and Trademark Office